United States Patent [19]

Heine et al.

[11] 4,285,239
[45] Aug. 25, 1981

[54] APPARATUS FOR MEASURING VARYING DENSITY OF A SLURRY FLOWING IN A PIPELINE

[76] Inventors: Otto R. Heine, 13372 Calle Colina, Poway, Calif. 92064; Peter M. Riede, 8257 Via Mallorca, La Jolla, Calif. 92037

[21] Appl. No.: 145,428

[22] Filed: May 1, 1980

[51] Int. Cl.³ .......................... G01N 9/06; G01F 1/74
[52] U.S. Cl. .................................. 73/434; 73/861.05; 177/145
[58] Field of Search .................... 73/434, 433, 861.05; 177/DIG. 9, 145

[56] References Cited

U.S. PATENT DOCUMENTS

| | | | |
|---|---|---|---|
| 1,905,558 | 4/1933 | Foote | 73/434 |
| 2,039,997 | 5/1936 | Hind | 73/434 |
| 2,613,530 | 10/1952 | Nichols | 73/434 |
| 2,669,118 | 2/1954 | Nichols | 73/434 |
| 3,143,887 | 8/1964 | Hathorn et al. | 73/434 |
| 3,320,791 | 5/1967 | Banks | 73/434 |
| 3,431,785 | 3/1969 | Love | 73/434 |
| 3,503,267 | 3/1970 | Kamekichi et al. | 73/434 |
| 3,812,723 | 5/1974 | Barron | 73/434 |

*Primary Examiner*—Donald O. Woodiel
*Attorney, Agent, or Firm*—Jackson, Jones & Price

[57] ABSTRACT

A densitometer apparatus is disclosed which is adapted for accurately measuring the density of a liquid and particularly of a slurry flowing in a pipeline. The apparatus includes a pipe section which is coupled to the rest of the pipeline by substantially friction and resistance free hydrostatic bearings in such a manner that the pipe section is able to move, at least to a limited extent, in a direction parallel with the earth's gravitational field. The weight of the pipe section is accurately measured together with the weight of the slurry or liquid contained therein by load cells, strain gauges or the like. A unique flow velocity meter is also disclosed. The flow velocity meter includes two densitometers positioned at a predetermined distance from one another on the pipeline, and measures the time it takes a density fluctuation pattern to travel from one densitometer to another.

27 Claims, 5 Drawing Figures

APPARATUS FOR MEASURING VARYING DENSITY OF A SLURRY FLOWING IN A PIPELINE

BACKGROUND OF THE INVENTION

1. Field of the Invention

The present invention is directed to an apparatus for accurately measuring the weight of a fluid flowing through a pipeline, and more particularly to an apparatus for accurately measuring the varying density of a slurry flowing through a pipeline. The present invention is also directed to an apparatus capable of measuring the flow velocity of a slurry flowing through a pipeline.

2. Brief Description of the Prior Art

Pipelines capable of transporting coal and various other mined minerals such as iron ore, in the form of a thick aqueous slurry have been known for a long time. These pipelines, particularly coal slurry pipelines, are presently gaining increasing importance in view of the world's increasing reliance on coal as a major energy source.

Such slurry pipelines for coal and other minerals vary greatly in length and diameter. The particulate size of the slurried coal or other solid mineral may also vary depending on the purpose and particular application of the transporting pipeline. In some instances the slurry predominantly contains rather fine particulate matter, while in some others the slurry may include relatively large, "chunk" sized particles. In case of coal slurry pipelines, the slurry may contain as much as 50% solid material by volume. As it is well known in the prior art, the density of slurries having rather large solid particles is usually not uniform throughout any cross-section of the pipeline; rather the heavier particles are settled toward the bottom of the pipeline. Furthermore, the average density of the slurry passing through any given cross section of the pipeline often varies as a function of time.

In light of the above, it has become standard practice in the art to determine the amount of coal or other solid mineral passing through any given point on the pipeline by measuring and monitoring the average density of the slurry as a function of time. This is accomplished in the prior art either by use of nuclear densitometers or by devices which measure the weight of a given pipe section containing the slurry flowing therethrough. Both nuclear densitometers and the weight measuring type densitometers, however, suffer from certain inherent shortcomings.

Nuclear densitometers work rather poorly when the density of the slurry is not uniform throughout the cross section of the pipe. The prior art weight measuring type densitometers on the other hand, are, generally speaking, unable to accurately determine the true weight of a given pipe section because of the inherent structural problem that the pipe section must be physically coupled to the pipeline. Various types of flexible joints were used for this purpose in the prior art, and such prior art density or weight measuring devices are described in U.S. Pat. Nos. 3,503,267; 3,320,791; 688,388; 2,039,997; 2,613,530; 2,669,118; 3,812,723; 3,143,887 and 1,905,558.

The joints of these prior art devices, however, negatively affect the accuracy of the measured weights and densities because of their usually nonlinear bending stiffness. The above cited patents indicate that significant effort was devoted in the prior art to increase the accuracy of weight measuring type densitometers, and that, in spite of this effort, truly accurate measurements have, up to the present, not been possible.

SUMMARY OF THE INVENTION

Accordingly, it is an object of the present invention to provide an apparatus for accurately measuring the weight of a pipe section wherein a liquid, and more particularly a slurry, is flowing.

It is still another object of the present invention to provide an apparatus which is adapted for accurately measuring the density and the velocity of a slurry flowing through a pipe.

These and other objects and advantages are attained by a densitometer apparatus or device having a pipe section linearly coupled to a pipeline with hydrostatic bearings. The pipeline carries a liquid, or more particularly a slurry, the density of which usually varies as a function of time.

The weight of the pipe section is measured by conventional devices such as load cells, strain gauges or the like. The accuracy of the readings is very favorably influenced by the hydrostatic bearings which allow, at least to a limited extent, motion of the pipe section in the direction parallel with the earth's gravitational field in a substantially frictionless, unresisted manner.

In one preferred embodiment of the present invention two densitometers are provided in the pipeline at a predetermined, known distance from one another. The time dependent fluctuation of the density of the slurry is monitored and recorded by both densitometers. A suitable microprocessor or like device is provided to compare density fluctuation patterns measured by the two densitometers and to identify identical patterns observed by the two densitometers within a brief time period. The microprocessor or like device computes the velocity of the flow from the time it takes a given fluctuation pattern to travel between the two densitometers.

The several features of the present invention can be best understood together with further objects and advantages from the following description taken together with the accompanying drawings in which like numerals indicate like parts.

DESCRIPTION OF THE PREFERRED EMBODIMENTS

The following specification taken in conjunction with the drawings set forth the preferred embodiments of the present invention in such a manner that any person skilled in the art of designing densitometers for flowing liquids and in the art of designing hydrostatic bearings can use the invention. The embodiments of the invention disclosed herein are the best modes contemplated by the inventors for carrying out their invention in a commercial environment, although it should be understood that various modifications can be accomplished within the parameters of the present invention.

Figure 1:
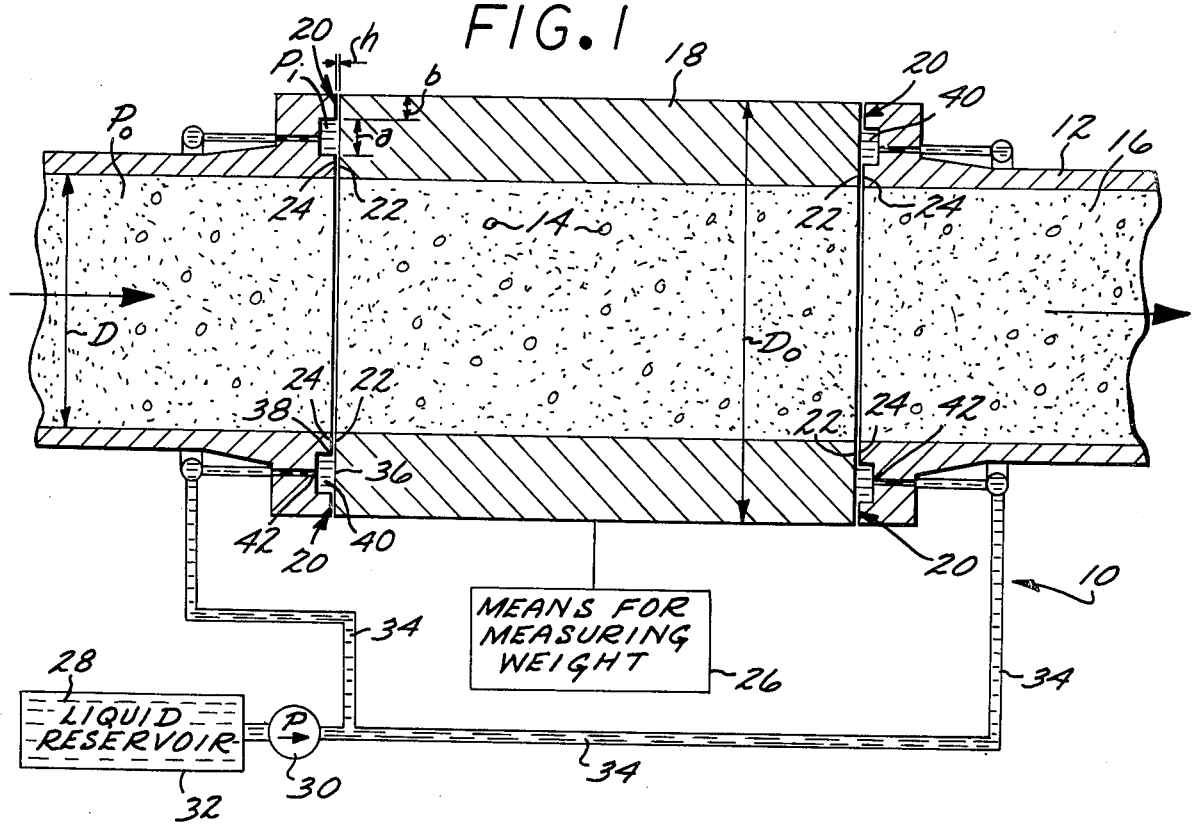
FIG. 1 is a diagrammatic cross sectional view illustrating the principle of operation of the densitometer of the present invention.

Referring now to the drawing Figures and particularly to the diagrammatic view of FIG. 1, the principle of operation of the novel density measuring device or densitometer 10 is disclosed.

The novel densitometer 10 of the present invention is particularly adapted for accurately measuring the density of a slurry of coal or other mineral flowing in a pipeline, although it is also suitable for measuring the density of various other liquids flowing in a pipeline. As it was mentioned in the introductory portion of the present patent application, accurately measuring the density of a rather thick slurry flowing in a pipeline, and particularly the measuring of the density of coal or other mineral slurries is of particular importance in the mining and the energy related industries. Accordingly, the densitometer 10 of the present invention will be principally described in conjunction with its application in association with a coal pipeline. Nevertheless, it should be expressly understood that the scope of the present invention is not limited by the materials, solid or liquid which may be transported in a pipeline.

Still referring to the diagrammatic view of FIG. 1, a pipeline 12 is shown wherein a slurry of coal particles 14 is transported in a liquid medium 16. The slurry may include particles of relatively uniform particle size, or may include some small particles as well as larger "chunk" sized particles. The liquid medium 16 which transports the particles 14 may be water or other liquid. Water is almost exclusively used in coal slurry and mineral slurry pipelines. In some applications, however, a hydrocarbon liquid medium may be employed for transporting coal particles. The scope of the present invention is, of course, not limited by the nature of the liquid medium 16.

In accordance with the present invention, the pipeline or pipe 12 includes a pipe section 18 which preferably has the same inner diameter as the pipe 12. In this regard, it is noted that the scope of the present invention is not limited by the diameter of the pipeline or pipe 12; generally speaking the densitometer 10 is well adapted for measuring the density of liquids and slurries flowing through pipelines of 2 to 24 inches in internal diameter. The length of the pipe section 18 is preferably 1–5 times the diameter of the pipeline 12.

As a principal feature of the present invention a pair of hydrostatic bearings or interfaces 20 are provided between the ends 22 of the pipe section 18 and the adjoining ends 24 of the pipeline or pipe 12. Hydrostatic bearings or interfaces are well known in the art and are often used in applications where a substantially frictionless interface is desired between two moving parts. For this reason, the nature of hydrostatic bearings or interfaces need not be generally described here in detail although for the sake of a full understanding of the present invention a brief description is provided.

Thus, a hydrostatic bearing includes at least two complementary precision formed surfaces. The two surfaces are separated from one another by a fluid layer or film which is supplied to the bearing at a sufficient pressure so as to separate the two surfaces from actual contact with one another. The fluid, which is hereinafter referred to as the hydrostatic fluid so as to distinguish it from the liquid or slurry flowing in the pipeline 12, is supplied by a pump. The pump usually supplies the hydrostatic fluid to the bearing through an appropriate flow restrictor such as a capillary opening. When the bearing is in operational equilibrium the amount of hydrostatic fluid lost from the bearing by outflow equals the amount of hydrostatic fluid supplied to the bearing by the pump through the flow restrictor. The typical size of a gap between the two precision formed surfaces which is filled by the hydrostatic fluid under pressure is usually in the 0.0002–0.002 inch range.

The specific structure of hydrostatic bearings usually includes at least one indentation or pocket. The pocket is provided in one of the complementary precision formed bearing surfaces and the hydrostatic fluid is usually directly supplied into the pocket through the capillary opening. As will become readily apparent from the ensuing description, the hydrostatic bearings utilized in the novel densitometer 10 of the present invention are, generally speaking, constructed in accordance with the above summarized principles.

Referring again to FIG. 1, the hydrostatic bearings 20 which couple the pipe section 18 to the pipeline 12 are shown to be disposed in substantially vertical positions. As a result, the pipe 18 is capable of moving, at least to a limited extent, practically without friction or resistance in a direction parallel with the earth's gravitational field. A suitable weight measuring and recording device is operatively attached to the pipe section 18 to continuously measure and record its weight. The weight measuring device bears the reference numeral 26 on the diagrammatic view of FIG. 1, and is labelled "Means for Measuring Weight" on the same.

The weight measuring device 26 may be of conventional type and construction. Its only relevant limitation is that it must be capable of measuring the varying weight of the pipe section 18 without requiring or allowing substantial displacement of the pipe section 18 in the vertical direction. This is, of course, necessary in order to keep the pipe section 18 and the pipeline 12 in operative positioning relative to one another so that flow of the slurry in the pipeline 12 not be disturbed and that the hydrostatic bearings 20 continue to operate efficiently. Certain types of load cells, strain gauges and particularly piezo type strain gauges are well adapted for this purpose.

In order to record the weight of the pipe section 18 the weight measuring device 26 is coupled to a recorder (not specifically shown) which in its simplest form may be a strip-chart recorder (not shown) or may be a suitable electronically operated recording and readout or printout device (not shown).

Still referring to FIG. 1, supply of a hydrostatic fluid 28 to the hydrostatic bearings 20 is shown diagrammatically. The hydrostatic fluid 28 which preferably comprises the same liquid, as the liquid medium flowing in the pipeline 12, is pumped by a pump 30 from a liquid reservoir 32 through suitable conduits or lines to the hydrostatic bearings 20. The hydrostatic bearings 20 comprise complementary precision formed surfaces formed on the respective ends 22 of the pipe section 18 and the ends 24 of the pipeline. These complementary precision formed surfaces respectively bear the reference numerals 36 and 38.

In accordance with standard practice in the hydrostatic bearing designing arts, an indentation or pocket 40 is provided in one of the precision formed surfaces 36 or 38 of each bearing 20, and the hydrostatic fluid 28 is directly supplied into the indentations or pockets 40 through a capillary opening 42.

It is essential for the operation of the densitometer 10 of the present invention that the pressure of the hydrostatic fluid 28 in the hydrostatic bearings 20 be higher than the pressure of the slurry or other liquid 16 flowing through the pipeline 12. In this regard, it is noted that the densitometer 10 of the present invention is most advantageously used in association with pipelines which typically have a slurry or liquid flowing therethrough at 100–1500 PSI. Coal slurry pipelines usually operate at approximately 1000 PSI. The pressure of the hydrostatic fluid 28 need to be only a few PSI higher than the pressure of the slurry 16. Since the pressure of the slurry or other liquid 16 in the pipeline 12 may fluctuate it is advantageous, however, to design the hydrostatic bearings 50 so that the pressure of the hydrostatic fluid 28 therein always exceed even the highest pressure which may occur in the slurry 16.

It will be readily appreciated by those skilled in the art, that while the hydrostatic bearings 20 are operational and are supplied with the hydrostatic fluid 28 under pressure, a small amount of the hydrostatic fluid 28 enters into the pipeline 12 and in a sense "contaminates" or "dilutes" the fluid medium 16 flowing therein. It can be calculated however, that the flow of the hydrostatic fluid 28 into the pipeline 12 is essentially negligible compared to the amount of slurry or liquid medium 16 flowing through the pipeline 12. For this calculation a formula is utilized which is well familiar to those skilled in the engineering arts and which describes under capillary laminar flow conditions the outflow of the hydrostatic fluid from a simple hydrostatic bearing of the type shown on FIG. 1.

Thus, in a pipeline and densitometer 10 of the type diagrammatically shown on FIG. 1, and having a pipeline internal diameter (D) of 16.0 inches, an external diameter (Do) of 22.0 inches, a pocket or indentation width (a) of 0.5 inches, a land width (b) of 1.25 inches, a gap (h) width of 0.0005 inches, a pressure of the hydrostatic fluid 28 in the pocket 40 (Pi) of 1200 PSI, an internal liquid medium 16 pressure (Po) of 1000 PSI, with the hydrostatic fluid being water at approximately 60° F. and therefore having a viscosity ($\mu$) of $1.39 \times 10^{-7}$ lb sec/inch$^2$, the flow (Qp) through each gap into the pipe 12 is given by the following equation $$Q_p = \frac{(D + b) \pi (P_i - P_o) h^3}{12 \, b\mu} \quad \text{(Equation 1)}$$

and is calculated to be a mere 0.65 inch$^3$/sec.

The flow (Qo) of the hydrostatic fluid from each gap to the outside of the pipe 12, is, on the other hand, determined by Equation 2 wherein the symbols represent the same as in Equation 1.

Thus, $$Q_o = \frac{(D_o - b) \pi P_i h^3}{12 \, b\mu} \quad \text{(Equation 2)}$$

and is calculated to be approximately 4.69 inch$^3$/sec.

It is readily apparent that compared to the volume of the liquid medium 16 flowing through the pipeline of 16 inches in internal diameter, the amount of the "diluting" hydrostatic fluid 28 is indeed negligible, and does not significantly or meaningfully affect the measured weight of the pipe section 18.

It should also be readily apparent from the above description that the substantially frictionless, resistance free hydrostatic bearings 20 allow such accurate measuring of the weight of the pipe section 18 which has hitherto been impossible in the prior art densitometers using various types of flexible couplings for supporting the pipe section. From the measured weight of the pipe section 18 which includes the weight of the slurry or liquid medium 16 momentarily contained therein, the density of the slurry or liquid medium 16 can readily be calculated. In fact, the weight measuring device 26 or the electronic computer and recorder (not shown) may be calibrated or programmed to provide a direct readout or printout of the measured slurry densities. This, of course, is in accordance with standard practice in the prior art.

From the total flow ($Q_T$) of the hydrostatic fluid 16 which was calculated above in accordance with Equations 1 and 2, it is possible to approximate the amount of power which is required to operate the densitometer 10 having the above noted specific dimensions.

Thus where $$Q_T = 2(Q_p + Q_o) = 10.68 \text{ inch}^3/\text{sec} = 2.77 \text{ gallons/minute}$$

and wherein the above amount is produced by a pump having a fifty percent efficiency ($\eta$), pressurizing the hydrostatic fluid 16 from ambient pressure to 1200 PSI (Pi), the amount of power consumed by the pump (HP pump) is given by Equation 3

$$HP \text{ pump} = \frac{P_i \times Q_T}{1.715 \, \eta} \quad \text{(Equation 3)}$$

and is calculated to be approximately 3.88 HP.

In light of the foregoing, it is already apparent that the novel densitometer 10 of the present invention has a relatively simple structure, consumes relatively little power and provides hitherto unattained accurate measurements.

Figure 2:
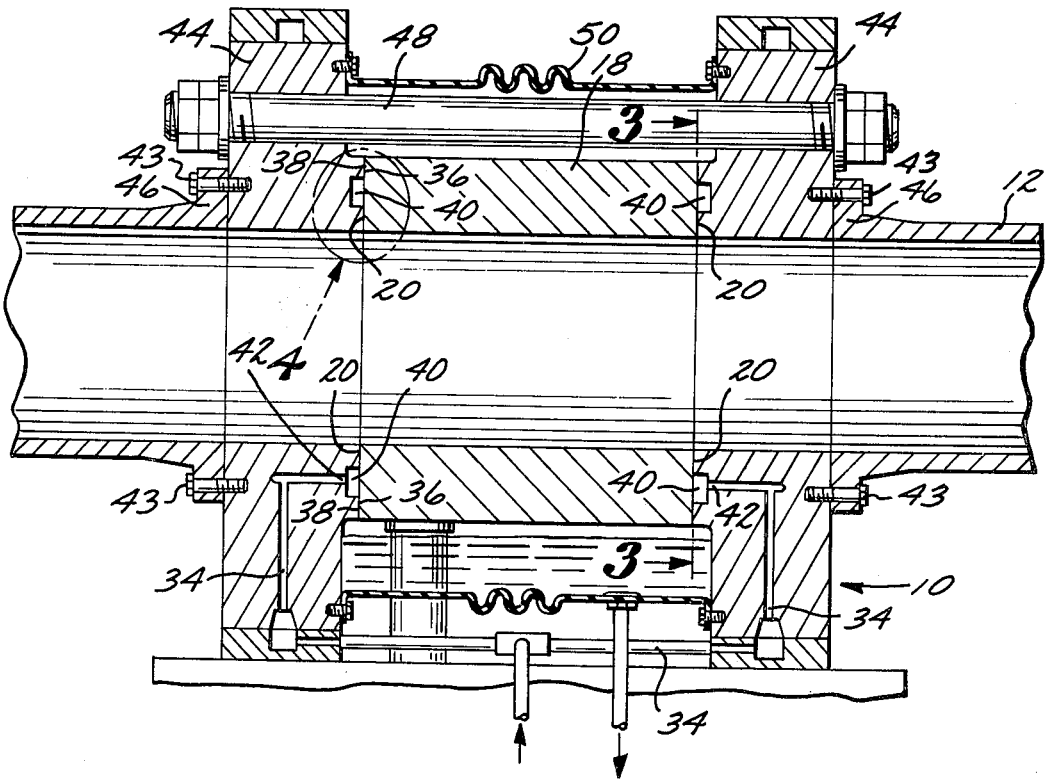
FIG. 2 is a cross sectional view of a preferred embodiment of the densitometer of the present invention.
Figure 3:
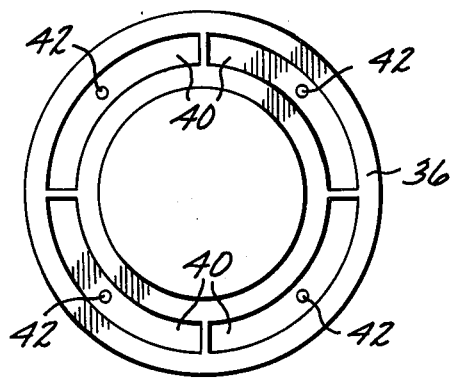
FIG. 3 is a view taken at lines 3—3 of FIG. 2.
Figure 4:
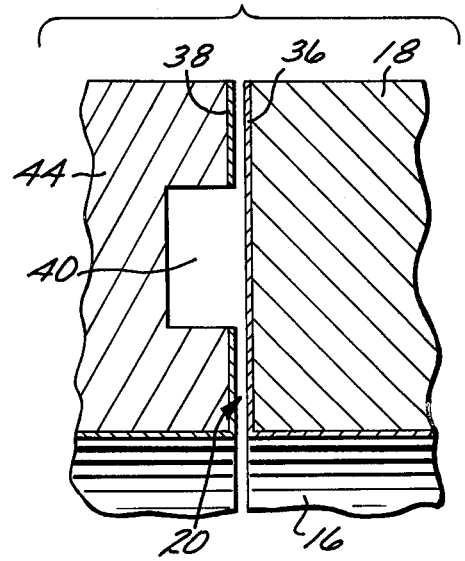
FIG. 4 is an enlarged view taken in the area indicated on FIG. 2.

Referring now to FIGS. 2–4 and particularly to the cross sectional view of FIG. 2, a preferred embodiment of the densitometer 10 of the present invention is disclosed in detail. The densitometer 10 operates in the above described manner, on the basis of the above described principles, and is specifically constructed so that it is relatively easily incorporated practically at any desired point in a pipeline 12.

The densitometer 10 includes a pair of flanges 44 which may be readily fastened by a plurality of bolts 43 to an existing pipeline 12. It is readily apparent from an inspection of FIG. 2 that in order to fasten the flanges 44 to a pipeline 12 it is merely necessary to remove a portion of the pipeline 12, and to provide the pipeline 12 with auxillary flanges 46 to which the flanges 44 are fastened by the bolts 43. The ends of the flanges 44 incorporate the precision formed surfaces 38. A pipe section 18 of a known weight having precision formed surfaces 36 which are complementary to and which interface with the precision formed surfaces 38 of the flanges 44, is positioned between the flanges 44. The pipe section 18 is held between the flanges 44 by a plurality of bolts 48 which interconnect the two flanges 44 with a predetermined force or tension. Only one of the interconnecting bolts 48 is shown on FIG. 2.

As an important feature of the preferred embodiment of the present invention, the predetermined force or tension of the interconnecting bolts 48 is set in such a manner that when no hydrostatic fluid 28 is supplied to the interfacing precision formed surfaces 36 and 38, no gap exists between these surfaces 36 and 38 and they are in physical contact with one another. Thus, when the densitometer 10 is not in operation, the slurry or other liquid medium 16 flowing in the pipeline does not leak out between the precision formed surfaces 36 and 38.

The precision formed surfaces 38 of the flanges 44 incorporate four indentations or pockets 40. These are of the same type as generally described above in connection with the principle of operation of the present invention, and are positioned in respective quadrant sections of the flanges 44, as is best shown on FIG. 3. A capillary opening 42 leads to each pocket 40, and the hydrostatic fluid 28 is introduced to each hydrostatic bearing 20 through the capillary openings 42.

A flexible bellow 50 interconnects the flanges 44, envelopes the pipe section 18 and serves as a reservoir to capture any hydrostatic fluid 28 which leaks out of the hydrostatic bearings 20 to the outside of the pipe section 18, when the densitometer is in operation. Hydrostatic fluid 28, in turn, is supplied under pressure into the capillary openings 42 by a pump 30 which is not shown on FIG. 2. The pump 30 supplies the hydrostatic fluid 28 through a conduit or line system 34 which includes at least one manifold 52, and which is partly incorporated in the flanges 44 themselves.

When operation of the densitometer 10 is desired, the pump 30 is energized. This results in the build-up of pressure in the hydrostatic fluid 28. When the pressure in the hydrostatic fluid 28 reaches the predetermined value set by the force or tension of the interconnecting bolts 48, the complementary precision formed surfaces 36 and 38 slightly separate from one another and the hydrostatic bearings 20 become operational. For example, when the average pressure of the slurry or other liquid medium in the pipeline 12 is approximately 1000 PSI and it is desirable to operate the hydrostatic bearings 20 at approximately 1200 PSI, the interconnecting bolts 48 may be set in such a manner that the hydrostatic bearings 20 become operational at 1100 PSI.

Actual measurement of the weight of the pipe section 18 including the weight of the slurry or other liquid medium 16 flowing therethrough, and computation of the slurry or liquid density is accomplished in the hereinbefore described manner.

Figure 5:
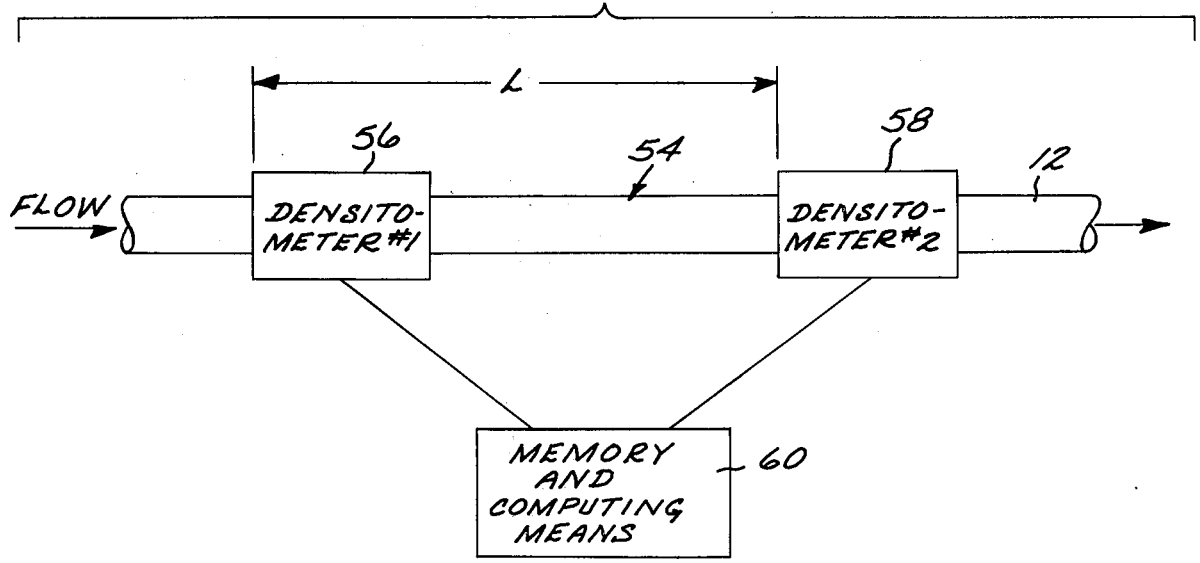
FIG. 5 is a diagrammatic view showing the principle of operation of a novel flow velocity meter which incorporates two densitometers of the present invention.
Figure 5:
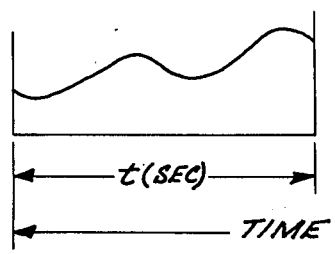
Figure 5:
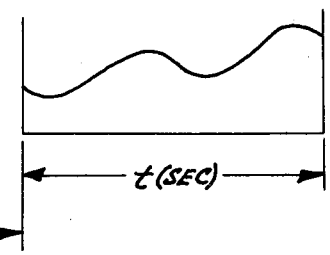

Referring now to the diagrammatic view of FIG. 5 utilization of two densitometers of the present invention for the purpose of measuring the velocity of a slurry 16 flowing in a pipeline 12, is disclosed. The densitometers when utilized in the hereinafter described manner, comprise a slurry flow velocity meter 54. The operation of the slurry flow velocity meter 54 is based on the phenomenon that in relatively thick slurries, such as coal water slurries flowing in a practical pipeline, the practically ever present density fluctuations exhibit certain patterns. These patterns change only slowly and gradually as the slurry flows along the length of the pipeline. For the purposes of the construction of the slurry flow velocity meter 54 of the present invention, the slurry density fluctuation patterns can be considered practically constant along any 50-100 feet portion of the pipeline 12.

Thus, in the herein described slurry flow velocity meter 54 two accurate densitometers 56 and 58 of the type previously described, are provided at a predetermined distance (L) from one another. Each densitometer 56 and 58 accurately measures the practically constantly changing density of the slurry 16. The respective outputs of the densitometers 56 and 58 are fed into, and stored in a suitable electronic device which on the diagrammatic drawing of FIG. 5 is labelled "Memory and Computing Means" and bears the reference numeral 60.

The electronic device 60 stores the density versus time functions or patterns measured by each densitometer 56 and 58 and continuously compares the stored patterns with one another. The electronic device 60 can be a special purpose computer or microprocessor and need not be described here in detail because its construction is well within the purview of the current state of the electronic arts. The electronic device 60 identifies when a pattern observed in the first densitometer 26 reaches the second densitometer 58 and measures the time required for the identified density pattern to travel the distance (L) between the two densitometers 56 and 58. From the measured time (T) the average flow velocity of the slurry 16 is readily calculated and may be exhibited by a continuous printout or readout of the electronic device 60. FIG. 5 illustrates the principle of the above described slurry flow velocity measurement and shows two substantially identical density-versus-time fluctuation patterns which may be observed by both densitometers 56 and 58 within a few seconds time span.

What has been described above is a novel densitometer adapted for the measuring of the density of a liquid flowing through a pipeline and particularly adapted for accurately measuring of the density of a relatively thick coal or mineral slurry flowing through a pipeline. Several modifications of the present invention may become readily apparent to those skilled in the art in light of the herein disclosed generic concepts. Accordingly, the scope of the present invention should be interpreted solely from the following claims.

What is claimed is:

1. A device for measuring the weight of a pipe section having a fluid flowing therethrough, the device comprising:
   a pipe adapted for having the fluid flowing therethrough;
   a section of said pipe having two ends, each end of the section being coupled to the pipe through a hydrostatic bearing operated by pressure of a hydrostatic fluid, said hydrostatic bearings providing a substantially frictionless interface between the pipe section and the pipe for a limited movement of the pipe section in the direction of the earth's gravitational force field, and
   first means for measuring the weight of the pipe section, said means operating without a substantial displacement of the pipe section relative to the pipe as the weight of the pipe section varies as a result of varying weight of the fluid flowing therethrough.

2. The invention of claim 1 further comprising second means for providing the hydrostatic fluid at the hydrostatic bearings at a pressure higher than a pressure of the fluid flowing through the pipe section.

3. The invention of claim 2 wherein each hydrostatic bearing comprises a pair of complementary precision formed surfaces, one of said surfaces being formed in the end of the pipe section and the other being formed in an adjoining end of the pipe, a gap being located between the precision formed surfaces, said gap being filled with the hydrostatic fluid under pressure.

4. The invention of claim 3 wherein one of said precision formed surfaces in each hydrostatic bearing includes at least one pocket, the hydrostatic fluid being supplied to the pocket by the second means through a flow restrictor.

5. The invention of claim 4 wherein one of said precision formed surfaces in each hydrostatic bearing includes a plurality of pockets.

6. The invention of claim 4 wherein the pipe section and the pipe is attached to one another by mechanical means, said mechanical means being adapted for reducing the gap in the two hydrostatic bearings to substantially zero when the pressure of the hydrostatic fluid is less than the pressure of the fluid flowing through the pipe, said mechanical means being also adapted for allowing the gap to occur between the respective adjoining precision formed surfaces when the pressure of the hydrostatic fluid reaches a predetermined value higher than the pressure of the fluid flowing through the pipe.

7. The invention of claim 6 wherein the pipe section is disposed horizontally.

8. A device for measuring density of a slurry flowing through a pipe, the device comprising:
a pipe through which the slurry may flow;
a section of the pipe, the section having two ends, each end being coupled to the pipe so that the slurry may flow through the section, each end of the section comprising a precision formed surface, ends of the pipe adjacent to the respective ends of the pipe section including precision formed surfaces respectively complementary to the precision formed surfaces provided on the ends of the pipe section, the adjacent precision formed surfaces on the ends of the pipe section and on the adjoining ends of the pipe comprising hydrostatic bearings;
first means for measuring the weight of the pipe section, said weight including the weight of the slurry flowing through the pipe section;
second means adapted for providing a fluid in the hydrostatic bearing at a pressure higher than the pressure of the slurry flowing in the pipe, and
third means for coupling and operatively positioning the pipe section to the pipe.

9. The invention of claim 8 wherein the third means are adapted for coupling the precision formed surfaces of the pipe section in contact with the respective complementary precision formed surfaces provided on the adjoining ends of the pipe when the fluid is not provided to the coupled precision formed surfaces at a pressure higher than the pressure of the slurry flowing in the pipe, and for allowing the precision formed surfaces to separate from one another thereby forming the hydrostatic bearings when the fluid is provided at a pressure higher than the pressure of the slurry flowing in the pipe.

10. The invention of claim 9 wherein a flange is provided substantially adjacent to each end of the pipe which is coupled to the pipe section, and wherein the third means include a plurality of bolts interconnecting the respective flanges.

11. The invention of claim 8 wherein one of the precision formed surfaces in each hydrostatic bearing includes at least one pocket, the fluid being supplied to the pocket by the second means.

12. The invention of claim 11 wherein one of the precision formed surfaces in each hydrostatic bearing includes a plurality of said pockets.

13. The invention of claim 8 further including computing means coupled to the first means, the computing means being adapted for computing the density of the slurry from the weight measured by the first means.

14. The invention of claim 8 wherein the second means comprise a pump and a motor operating the pump.

15. The invention of claim 8 wherein the pipe section is disposed substantially horizontally.

16. A device for measuring the density and flow velocity of a slurry flowing through a pipe, the device comprising:
a first and a second pipe section adapted to be incorporated in the pipe, the first and second pipe sections being located at a predetermined distance from another and positioned so that the slurry may flow first through said first section and thereafter through said second section, the first and second pipe sections being coup to the pipe through substantially frictionless hydrostatic bearings, allowing each pipe section to be displaced in a substantially frictionless manner to a limited extent relative to the pipe in a direction parallel with the earth's gravitational field;
first measuring means connected to each pipe section for measuring the weight of each pipe section, said weights including the weights of the slurry flowing through the pipe section;
second memory means connected to the first means for storing the measured weights or densities computed therefrom of each pipe section as a function of time whereby any slurry density fluctation travelling through the pipe is stored, and
third comparing and computing means connected to the second means for comparing with one another density versus time patterns measured and stored respectively at the first and second pipe sections and for computing the flow velocity of the slurry from the predetermined distance and from the time a given density versus time fluctuation pattern takes to travel from the first pipe section to the second pipe section.

17. The invention of claim 16 further comprising pump means for providing the hydrostatic bearings with a fluid a pressure higher than the pressure of the slurry travelling in the pipe.

18. The invention of claim 17 further comprising mechanical means for operatively positioning the first pipe section and the second pipe section relative to the pipe.

19. The invention of claim 18 wherein the mechanical means is adapted for allowing ends of each pipe section to slightly separate from contact with adjoining ends of the pipe when the fluid is provided by the pump means at a pressure higher than a predetermined pressure, said predetermined pressure being higher than the pressure of the slurry flowing in the pipe whereby the hydrostatic bearings become operational.

20. The invention of claim 16 wherein the first pipe section and the second pipe section are disposed substantially horizontally.

21. A device for measuring the density of a fluid flowing through a pipe, the device comprising:
a first flange adapted to be mechanically fastened to the pipe and having an opening to be positioned in substantial alignment with the inner diameter of the pipe and a precision formed surface;
a second flange adapted to be mechanically fastened to the pipe, and having an opening to be positioned in substantial alignment with the inner diameter of the pipe and a precision formed surface;

a pipe section having a precision formed surface at each end thereof, the precision formed surfaces of the pipe section being respectively complementary to the precision formed surfaces of the first and second flanges;

first means for fastening the pipe section between the first and second flanges so that the precision formed surfaces of the pipe section are disposed adjacent to the respective precision formed surfaces of the first and second flanges, said adjacent, complementary precision formed surfaces capable of comprising hydrostatic bearings when a hydrostatic fluid is supplied to them, the hydrostatic bearings allowing a substantially frictionless motion of the pipe section in a direction parallel with the earth's gravitational field, and second means for measuring the weight of the pipe section, said weight including the weight of the fluid which may flow through the pipe section.

22. The invention of claim 21 wherein one of the adjacent complementary surfaces comprising each hydrostatic bearing includes a pocket into which the hydrostatic fluid may be supplied under pressure.

23. The invention of claim 21 wherein one of the adjacent complementary surfaces comprising each hydrostatic bearing includes a plurality of pockets into which the hydrostatic fluid may be supplied under pressure.

24. The invention of claim 21 wherein the first means are adapted for positioning the precision formed surfaces of the pipe section in contact with the respective precision formed surfaces of the first and second flanges when a pressure of the hydrostatic fluid supplied of the adjoining complementary precision formed surfaces is less than a predetermined value, the first means also being adapted for allowing the respective adjoining complementary surfaces to slightly separate from one another when the pressure of the hydrostatic fluid supplied to the adjoining complementary precision formed surfaces is higher than a predetermined value whereby the hydrostatic bearings become operational.

25. The invention of claim 24 further comprising third pump means adapted for providing the hydrostatic fluid to the respective adjoining complementary surfaces at a pressure higher than the predetermined pressure.

26. The invention of claim 24 wherein the predetermined pressure is at least as high as the pressure of the fluid flowing in the pipe.

27. The invention of claim 24 wherein the first means includes a plurality of bolts connecting the first and second flanges with one another capturing the pipe section between the first and second flanges, the tension of the bolts being set to allow separation of the adjoining complementary precision surfaces when the hydrostatic fluid is supplied to the adjoining complementary precision surfaces at the predetermined pressure.

* * * * *

UNITED STATES PATENT AND TRADEMARK OFFICE
CERTIFICATE OF CORRECTION

PATENT NO. : 4,285,239
DATED : August 25, 1981
INVENTOR(S) : Otto R. Heine; Peter M. Riede It is certified that error appears in the above—identified patent and that said Letters Patent is hereby corrected as shown below:

Column 10, line 17, delete "coup" and insert --coupled--.

line 31, delete "fluctation and insert --fluctuation-

Column 12, line 16, delete "fluidto" and insert --fluid to--.

Signed and Sealed this

Eighth Day of December 1981

[SEAL]

Attest:

GERALD J. MOSSINGHOFF

Attesting Officer  Commissioner of Patents and Trademarks